United States Patent [19]

Brace

[11] Patent Number: 4,517,384

[45] Date of Patent: May 14, 1985

[54] PERFLUOROALKYL ALKYLENE VINYL SULFOXIDES AND SULFONES

[75] Inventor: Neal O. Brace, Wheaton, Ill.

[73] Assignee: Ciba-Geigy Corporation, Ardsley, N.Y.

[21] Appl. No.: 459,739

[22] Filed: Jan. 21, 1983

[51] Int. Cl.$^3$ .................. C07C 147/02; C07C 149/06
[52] U.S. Cl. ....................................... 568/27; 568/35; 560/129
[58] Field of Search .................................... 568/27, 35

[56] References Cited

U.S. PATENT DOCUMENTS

| 2,103,879 | 12/1937 | Ufer | 568/28 |
| 2,140,569 | 12/1938 | Ufer et al. | 568/28 |
| 3,428,687 | 2/1969 | Aichenegg et al. | 568/27 |
| 3,578,717 | 5/1971 | Mitsch et al. | 568/35 |

Primary Examiner—Donald G. Daus
Assistant Examiner—S. A. Gibson
Attorney, Agent, or Firm—Michael W. Glynn

[57] ABSTRACT

Perfluoroalkyl alkylene vinyl sulfoxides and sulfones of the formula

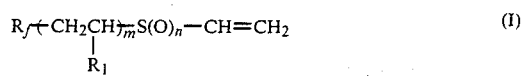

$$R_f(CH_2CH)_{\overline{m}}S(O)_n-CH=CH_2 \quad \text{(I)}$$
$$\hphantom{R_f(CH_2CH)_{\overline{m}}}|$$
$$\hphantom{R_f(CH_2CH)_{\overline{m}}}R_1$$

wherein $R_f$ is perfluoroalkyl of 3 to 18 carbon atoms, $R_1$ is hydrogen or lower alkyl, m is 1 to 3 and n is 1 or 2, intermediates thereof, methods for their preparation, and the uses of such compounds to render cellulosic, and natural and synthetic polyamide, materials hydrophobic and oleophobic are described.

4 Claims, No Drawings

PERFLUOROALKYL ALKYLENE VINYL SULFOXIDES AND SULFONES

GENERAL DESCRIPTION OF THE INVENTION

The instant invention relates to new and useful perfluoroalkyl-alkyl vinyl sulfoxides and sulfones, intermediates thereof, methods of preparation, and methods of use thereof to render cellulosic, and natural and synthetic polyamide, materials hydrophobic and oleophobic.

Accordingly, it is an object of the present invention to provide the artisan with new and useful perfluoroalkyl-alkyl vinyl sulfoxides and sulfones and telomers, polymers and co-polymers thereof.

It is a further object of the present invention to provide the artisan with methods of preparation of such perfluoroalkyl-alkyl vinyl sulfoxides and sulfones, as well as valuable intermediates in the preparation thereof.

It is yet a further object of the present invention to provide useful compositions and methods of rendering hydrophobic and oleophobic cellulosic, and natural and synthetic polyamide, materials using such compositions containing the perfluoroalkyl-alkyl vinyl sulfoxides and sulfones, or containing telomers, polymers or co-polymers thereof.

DETAILED DESCRIPTION OF THE INVENTION

One embodiment of the instant invention relates to compounds of the formula $$R_f\text{---}(CH_2\text{---}CH)_m\text{---}S(O)_n\text{---}CH=CH_2 \quad (I)$$
$$\qquad\qquad\quad |$$
$$\qquad\qquad\quad R_1$$

wherein
$R_f$ is perfluoroalkyl of 3 to 18 carbon atoms;
$R_1$ is hydrogen or lower alkyl;
m is 1 to 3; and
n is 1 or 2.

Preferably, $R_f$ is perfluoroalkyl of 4 to 16 carbon atoms. Also a mixture of $R_f$ groups as defined above may be present. Most preferred mixtures are those wherein the $R_f$ group has a range between about 4 and 12 carbon atoms with an average chain length between about 6 and 10 carbon atoms.

$R_1$ is preferably hydrogen or methyl, most preferably hydrogen; m is preferably 1 or 2, most preferably 1; and n is preferably 2.

The compounds of formula I are advantageously prepared by HX elimination of an intermediate of the formula $$R_f\text{---}(CH_2CH)_m\text{---}S(O)_n\text{---}CH_2\text{---}CH_2\text{---}X \quad (II)$$
$$\qquad\qquad |$$
$$\qquad\qquad R_1$$

wherein X is a nucleofugic leaving group, and $R_f$, $R_1$, m and n are as defined above, to form the corresponding compound of formula I.

Suitable leaving groups include halo, hydroxy, lower alkoxy, lower acyloxy, alkali metal sulfato and the like.

The term, "lower", as used herein, refers to groups having 1 to 5 carbon atoms, in the alkyl group thereof.

Halo is preferably chloro, bromo or iodo.

Advantageously, the elimination reaction is conducted at temperatures between about 0° and 100° C., in the presence of inert solvent, such as an acetone/water mixture, tetrahydrofuran, di-n-propyl ether, and the like, and where HX is an acid, preferably in the presence of an acid acceptor, such as triethylamine, N,N-dimethyl benzylamine, sodium hydroxide and the like.

Preferably, X is hydroxy, chloro, alkali metal sulfato or acetoxy, most preferably hydroxy, chloro or acetoxy.

Those compounds of formula I wherein n is 1 or 2 can be prepared from the corresponding thioether of the formula $$R_f\text{---}(CH_2CH)_m\text{---}S\text{---}CH_2CH_2X \quad (III)$$
$$\qquad\qquad |$$
$$\qquad\qquad R_1$$

where $R_f$, $R_1$, m and X are as defined above, by oxidation with an organic or inorganic peroxide, preferably hydrogen peroxide, in a diluent, such as acetic acid, at a temperature between about 10° C. and 100° C. If the sulfoxide is desired, i.e. where n=1 in formula II, then advantageously about one mole of peroxide is reacted per mole of the compound of formula III. If the sulfone product is desired, i.e. where n=2 in formula II, then at least 2 moles of peroxide material is advantageously added for each mole of the compound of formula III present.

An excess of peroxide in the latter case is often desirable to insure an optimized yield of the sulfone product.

The compounds of formula III can advantageously be prepared by a variety of techniques.

For example, compounds of formula III where X is lower acyloxy or halo, can advantageously be prepared by reacting a mercaptan of the formula $$R_f\text{---}(CH_2CH)_m\text{---}SH \quad (IV)$$
$$\qquad\qquad |$$
$$\qquad\qquad R_1$$

where $R_f$, $R_1$ and n are as defined above with a vinyl alkanoate or halide of the formula $$CH_2=CH\text{---}X \quad (V)$$

where X is lower acyloxy or halo, in the presence of a free radical initiator, preferably an azo compound such as azo-bis-2-methylpropionitrile, optionally in the presence of an inert diluent or solvent, at a temperature between about −100° C. and 100° C., and recovering the corresponding compound of formula III.

As an alternate method, the aforementioned mercaptan of formula IV can be reacted with a compound of the formula $$X_1\text{---}CH_2CH_2\text{---}X$$

where $X_1$ is chloro or bromo, and X is halo, hydroxy, lower acyloxy or lower alkoxy, in the presence of a basic agent, such as an alkali metal hydroxide, advatangeously in the presence of inert diluent, at a temperature between about 0° C. to 100° C. Optionally, the reaction can take place in a heterogeneous aqueous/organic phase in the presence of a phase transfer catalyst, such as benzyl trimethyl ammonium chloride, tricaprylmethyl ammonium chloride, didodecyl dimethyl ammonium bromide or the like.

The perfluoroalkyl alkylene vinyl sulfoxides and sulfones according to formula I can be telomerized or polymerized alone or in combination with conventional monomers to obtain polymeric product having advantageous oil and water repellent properties.

Thus, for example, the compounds of formula I can be caused to form polymers or copolymers, by polymerization techniques known per se. Thus, the compounds of formula I can, for example, be telomerized or polymerized in solution, e.g. in the presence of an organic solvent, such as benzene, toluene, xylene or the like, in the presence of actinic light, e.g. ultraviolet light, or a free radical catalyst, such as azo-bis-2-methylpropionitrile.

If desired, the compounds of formula I may be copolymerized with other monomers, including vinyl compounds, such as vinyl acetate and vinyl chloride; alkenes, such as ethylene, isopropylene, styrene; acrylates and methacrylates such as methyl acrylate, butyl acrylate, methyl methacrylate and the like, etc. The nature of such other monomers is not critical, and are sometimes found to be advantageous extenders of the desirable oleophobic and hydrophobic properties exhibited by the polymers of the monomers of formula I.

Suitable cellulosic and natural and synthetic polyamide materials include, for example, paper articles, paper pulp, cotton, regenerated cellulose, jute and the like, leather, feathers, nylon fibers, etc.

Thus, materials treated may be in the form of fibers, pulp, film, solution or yarn fabrics. The materials are advantageously coated with the polymer or copolymer of the compound of formula I to impart oil and water repellency to said materials.

Alternatively, a solution or emulsion of the compound of formula I may be applied to the surface of the material by any convenient means, such as dipping, padding or the like, and polymerized in situ, optionally in the presence of an alkaline catalyst, such as an alkali metal hydroxide, and a free radical catalyst, if desired, to form a polymer firmly bonded to the material substrate.

Suitable solvents for the compounds of formula I and the telomers, polymers and copolymers thereof include conventional organic solvents such as ketones, e.g. acetone, hydrocarbons, e.g. benzene, toluene and xylene, ethers, e.g. tetrahydrofuran, haloalkanes, e.g. chlorinated ethanes, fluorinated ethanes and the like. Also aqueous and aqueous/organic emulsions may be employed by the use of conventional surfactants and the like. Application temperatures may vary depending upon the application technique, but will ordinarily range between about 10° C. and 120° C., under ambient or superatmospheric pressure.

The following examples are for illustrative purposes only and are not intended to limit the scope of the invention.

EXAMPLE 1

Reaction:

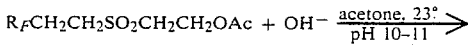

$(R_F = C_6F_{13})$

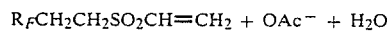

2-(Perfluorohexyl)ethanyl Vinyl Sulfone 2-(Perflurohexyl)ethanyl-2-acetoxyethanyl sulfone (10.27 g, 0206 mole), 100 ml of acetone and 10 ml of water was stirred by magnet bar in an Erlenmeyer flask, fitted with an Hydrogen ion electrode attached to a Sargent-Welch pH meter. At 23° the pH was brought to 10.4 by adding 0.25M NaOH solution (62 ml) and kept in the pH range of 10.57–11.07 (44 ml of base) during 8 h at 22°–23°. The solution remained slightly cloudy throughout. On standing overnight the pH dropped to 8.97; thus, base (2.00 ml) was added at pH 10.2–11.4, until it was constant at pH 10.9. Acetone was evaporated off in an open beaker at 55°–62°, the mixture cooled to 25°, and solid product precipitated, 8.60 g (dry); mp 58°–60°, 95% of theory for 2-(perfluorohexyl)ethanyl vinyl sulfone. The product was recrystallized from hot carbon tetrachloride (8.0 g in 40 ml, filtered hot); fractions obtained were 6.16 g, mp 60°–61°; 0.55 g, mp 60°, and 0.10 g (81.2% recovery). An infrared spectrum (Mineral oil mull) showed bands at 3060, 3030 (HC=), 1610 (CH=CH), 1090, 1075 (SO$_2$), 990, (960) and 920 cm$^{-1}$. NMR was consistent with the structure of the product: at 2.60 ppm, a complex multiplet, 2 protons (CH$_{2A}$); at 3.24 ppm, complex multiplet, 2 protons, (CH$_{2B}$); at 6.24 ppm, 2 sets of resonances, 3 protons, (CH$_C$=CH$_D$H$_E$). R$_F$CH$_{2A}$CH$_{2B}$SO$_2$CH$_C$=CH$_D$H$_E$.

Anal. Calcd for C$_{10}$H$_7$F$_{13}$O$_2$S: C, 27.4; H, 1.61; F, 56.4; S, 7.32. Found: C, 27.4; H, 1.6; F. 56.2; S, 7.7.

EXAMPLE 2

Reaction:

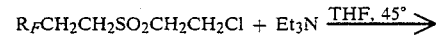

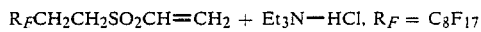

2-(Perfluorooctyl)ethanyl Vinyl Sulfone 2-(Perfluorooctyl)ethanyl 2-chloroethanyl sulfone (R$_F$=C$_8$F$_{17}$, 5.74 g, 10.0 mmole) was dissolved in 40 ml of tetrahydrofuran (THF) at 45°, while stirring in a constant temperature oil bath. Triethylamine (1.52 g, 2.10 ml, 15.0 mmole) in 10 ml of THF was added and an exotherm carried the temperature to 51°. A precipitate of white solid triethylammonium chloride immediately began to form. After 1 hour at 45° the slurry was filtered while hot (Buchner funnel), rinsed with diethyl ether twice, and the clear filtrate evaporated on a rotary evaporator. The dry solid Et$_3$N HCl weighed 1.35 g, 98.8% of theory. The evaporated solid 2-(perfluorooctyl)ethanyl vinyl sulfone was taken to 40°/15 mm and weighed 5.38 g, 100% of theory; mp sinter 92° melt 93°–94.5°. The sulfone was heated further to 155° without evidence of decomposition. The sulfone was soluble in chloroform, and insoluble in carbon tetrachloride, benzene or ligroine (bp 60°–70°). The sulfone dissolved in hot benzene, but was insoluble in hot ligroine. A 1.00 g sample was dissolved in 8.0 ml of benzene by heating on a steam bath, with care to prevent foaming over; 8.0 ml of ligroine was added and the clear, colorless solution when cool gave 0.77 g of solid, mp sinter 94° melt 95°–96°. When concentrated to 4.0 ml volume a fraction, 0.11 g, mp 96°–97° was obtained. The original sample gave a single spot in TLC analysis. The infrared spectrum was identical to that of the C$_6$ homolog of Example 1. The NMR spectrum was consistent with the proposed structure and resembled closely that obtained from the $C_6$ homolog.

Anal. Calcd for $C_{12}H_7F_{17}O_2S$: C, 26.8; H, 7.06; F, 60.0; S, 5.96. Found: C, 26.5; H, 1.5; F, 60.2; S, 6.8.

EXAMPLE 3

2-(Perfluorohexyl)ethanyl Vinyl Sulfone 2-(Perfluorohexyl)ethanyl 2-chloroethanyl sulfone (4.75 g, 10.0 mmole) was dissolved in 25 ml of THF at 30°, and triethylamine (1.52 g, 15.0 mmole) in 10 ml of THF was added in one minute. A white precipitate formed, and was filtered (1.37 g). The solvent was stripped carefully, as some foaming occurred.

The sulfone (4.33 g, 100% of theory), had mp of 60°–62°. A 1.00 g-sample was recrystallized from 15 ml of hot ligroine (bp 60°–70°). Fractions obtained were 0.90 g, mp sinter 59° melt 60°–61°, and 0.07 g, mp 60°–61°. TLC analysis of the original sample gave a single spot.

EXAMPLE 4

2-(Perfluorodecyl)ethanyl Vinyl Sulfone 2-(Perfluorodecyl)ethanyl 2-chloroethanyl sulfone (3.37 g, 5.00 mmole) and tetrahydrofuran (25 ml) were stirred at 50° and triethylamine (1.01 g, 10.0 mmole) was added, giving an exotherm to 52°. After a half hour at 50°, the reaction mixture was evaporated off and the white solid (3.83 g) was suspended and stirred in water (50 ml). The solid was collected and dried (2.96 g), mp (sinter 115°) 117°–121°. A sample recrystallized from benzene and acetone gave white solid mp 123°–125° (2.18 g). An IR Spectrum (Nujol mull) gave bands at 3120, 3040, 1600, 970 and 930 cm, characteristic of 2-(perfluorodecyl)ethanyl vinyl sulfone. The yield was 92.7% of theory.

EXAMPLE 5

Reaction:

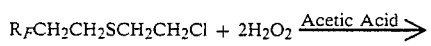

Preparation of 2-(Perfluorohexyl)ethanyl 2-Chloroethanyl Sulfone 5-(Perfluorohexyl)-3-thia-1-chloropentane (6.16 g, 13.9 mmole) was stirred by magnet bar and dissolved in 5 ml of acetic acid at 50°. Hydrogen peroxide (4.42 g, 39.0 mmole, Fisher Certified, 30% aqueous solution) in 10 ml of acetic acid was added dropwise. The reaction mixture was heated to 70° for 2 h; a sample had mp 104°–105.5°. After 80 min at 70° and 30 min at 90°, the mixture was evapd off at room temperature, to a white solid, wt, 6.48 g (98% of theory), mp 101°103°. Recrystallized from benzene (40 ml) at 68° gave 7, 6.09 g, mp 105°–105.5°; 0.22 g and 0.04 g, mp (sinter 103°) 105°–106°. An IR spectrum (HCCl$_3$) gave bands at 1430, 1400, 1065, 1050, 1015, 955, 935 and 900 cm$^{-1}$ that were characteristic of the substance. An NMR spectrum gave proton resonances at 2.80 ppm, a complex pattern, 2 protons, $CH_{2A}$; at 3.42 ppm, a complex pattern, 4 protons, $CH_{2B}$ and $CH_{2C}$; and at 3.97 ppm, a triplet, 2 protons, $CH_{2D}$; of $R_FCH_{2A}CH_BSO_2CH_{2C}CH_{2D}Cl$.

Anal. Calcd for $C_{10}H_8F_{13}ClO_2S$: C, 25.3; H, 1.7; F, 52.0; Cl, 7.47; S, 7.0. Found: C, 25.2; H, 1.4; F, 52.1; Cl, 7.2; S, 7.0.

EXAMPLE 6

Preparation of 2-(Perfluorooctyl)ethanyl 2-Chloroethanyl Sulfone 5-(Perfluorooctyl)-3-thia-1-chloropentane (5.18 g, 9.54 mmole) in 10 ml of acetic acid and hydrogen peroxide (3.40 g, 30.0 mmole) in 5 ml HOAc were allowed to react under conditions used in Example 5. The dry product weighed 5.34 g (97.4% of theory) and had mp 130°–131°. A sample recrystallized from benzene, mp 132°–132.5°. An IR spectrum (CHCl$_3$ slurry) gave bands at 1435, 1400, 1090, 1070, 1055, 1020, and 940 cm$^{-1}$.

Anal. Calcd for $C_{12}H_8F_{17}ClO_2S$: C, 25.08; H, 1.40; F, 56.20; Cl, 6.17; S, 5.58. Found: C, 25.0; H, 1.4; F, 56.2; Cl, 6.3; S, 6.0.

EXAMPLE 7

2-(Perfluorodecyl)ethanyl 2-Chloroethanyl Sulfone 5-(Perfluorodecyl)-3-thia-1-chloropentane (5.00 g, 7.78 mmole) in 10 ml of acetic acid and hydrogen peroxide (3.40 g, 30.0 mmole) in 5 ml of acetic acid were allowed to react under conditions used in Example 5, but for reaction at 90° for 15 h. A white solid formed in the reaction that was scraped out of the flask, 5.0 g (95% of theory); mp 147°–148°. A sample recrystallized from benzene, mp 147°–149°. Sintering was observed in both samples at about 141°–143°.

EXAMPLE 8

Reaction:

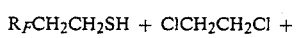

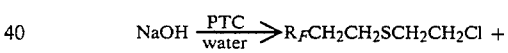

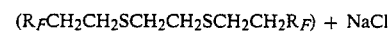

5-(Perfluorohexyl)-3-thia-1-chloropentane

A solution of 2-(perfluorohexyl)ethanethiol (7.60 g, 20.0 mmole) in 50 ml of water containing sodium hydroxide (0.80 g, 20 mmole) was added during 1.5 h to 1,2-dichloroethane (61.75 g, 62.4 mmole, 50 ml) and "Aliquat 336" (0.13 g, 0.29 mmole, General Mills tricaprylmethylammonium chloride), while stirring by means of a paddle stirrer in a 200 ml, round bottom flask at 25°–27°. Two liquid phases were present. After 5 hours a sample of the organic layer was dried (MgSO$_4$) and GC analysis [6-ft SE 30 silicone oil on Chromosorb WA, temperature programmed from 150°–180°, 33.5 ml/min of Helium flow] showed 1,2-dichloroethane (93.5%), title compound (6.32%) and unknown (0.3%). The ratio of the last two peaks was 97.6/2.4. After 6 h, the layers were separated, the organic layer dried and distilled in a 16-inch spinning band column, to give 1,2-dichloroethane, bp 76°–79°, 58.0 g; and 5-(perfluorohexyl)-3-thia-1-chloropentane, bp 80°–81°/1.75 mm, $n^{25}{}_D$ 1.3717, 7.15 g (80.7% of theory). A crystalline residue (0.81 g) remained.

Anal. Calcd for $C_{10}H_8F_{13}ClS$: C, 27.1; H, 1.8; F, 55.8; Cl, 8.0; S, 7.2. Found: C, 27.4; H, 1.7; F, 55.7; Cl, 8.0; S, 7.5.

EXAMPLE 9

5-(Perfluorooctyl)-3-thia-1-chloropentane 2-(Perfluorooctyl)ethanethiol (48.75 g, 0.1018 mole; 0.78% $C_6$, 95.6% $C_8$ and 0.84% $C_{10}$ $R_F$ groups) was added, while stirring under nitrogen, to sodium hydroxide (4.58 g, 0.165 mole) in water (75 ml). The thick slurry was diluted with water (100 ml) and added in portions during a half hour to 1,2-dichloroethane (309 g, 3.12 mole, 250 ml) and "Aliquat 336" (0.50 g. 1.1 mmole) while stirring in a 500-ml, rb, 3-necked flask fitted with a paddle stirrer, nitrogen purge inlet tube and condenser. An exotherm carried the temperature from 24° to 28°. After 7 hours at ambient temperature the layers were separated, and the aqueous layer extracted with 1,2-dichloroethane (20 ml). The organic layers were combined and filtered from an insoluble solid (3.19 g, mp (sinter 67°) 68°–72°). Unreacted 1,2-dichloroethane was removed by distillation and the residual oil (81.45 g) was distilled in a 16-inch spinning band column. Fractions obtained were: I, bp 98°–104°/3.8 mm, 1.73 g; II, bp 104°–105°/3.8 mm, 43.25 g, mp 39°–40°; and III, bp 85°/0.75–0.30 mm, 2.10 g. The total yield of $C_8F_{17}CH_2CH_2SCH_2CH_2Cl$ was 86.8% of theory. A residue of 3.02 g remained in the pot flask. In TLC analysis Fractions I, II and III gave only $C_8F_{17}CH_2CH_2SCH_2CH_2Cl$.

Anal. Calcd for $C_{12}H_8F_{17}ClS$: C, 26.6; H, 1.48; F, 59.5; Cl, 6.9; S, 5.9. Found: C, 26.6; H, 1.6; F, 59.4; Cl, 6.9; S, 6.5.

EXAMPLE 10

5-(Perfluoroalkyl)-3-thia-1-chloropentane ($R_F = C_4$, 0.8%; $C_6$, 34.1%; $C_8$, 35.8% $C_{10}$, 22.7%; $C_{12}$, 6.5% and $C_{14}$, 0.5%). A 2-perfluoroalkylethanethiol mixture (46.70 g, 0.10 mole, as llisted above), a solution of sodium hydroxide (4.60 g, 0.115 mole) in 200 ml of water and "Aliquat 336" (0.23 g, 0.52 mmole) were stirred under nitrogen purge as in the reactions described above, while 1,2-dichloroethane (450.8 g, 4.55 mole) was added at 25°. The two layers were stirred for 6.5 h, the last two h heated to 50°. Work-up of the reaction product mixture gave distilled fractions as follows:

I, bp 70°–82°/2.5 mm, 14.64 g; II, bp 80°–96°/1.5 mm, 5.37 g; III, bp 91°–102°/2.5 mm, 12.93 g; IV, bp 92°–106°/0.35–0.30 mm, 6.65 g; and residue, 2.50 g. Fractions I to III were mixtures of $C_4$ to $C_8$ (chiefly), while fraction IV was chiefly $C_{10}F_{21}CH_2CH_2SCH_2CH_2Cl$. An insoluble solid, 6.86 g, mp (sinter 96°) 105°–115°, was filtered from the organic layer before distillation.

EXAMPLE 11

5-(Perfluorooctyl)-3-thia-1-chloropentane 2-(Perfluorooctyl)ethanethiol ($R_F = C_8F_{17}$, 4.80 g, 10.0 mmle) and 1,2-dichloroethane (29.67 g, 300 mmole) and 10 ml of water was stirred by magnet bar under nitrogen at ambient temperature, while sodium hydroxide (0.67 g, 16.7 mmole) in 20 ml of water was added dropwise during a half hour. An exotherm carried the temperature from 24.0° to 25.2°. A thick, white slurry was formed. After 5 hours of stirring at 23.5°, the white slurry had not separated into two liquid layers as in the procedures used above. Stirring was continued for 29 hours and a sample removed for analysis. After 39 hours the thick white paste was made acidic by the addition of 5.0 ml of 6N hydrochloric acid, and the white solid collected on a Buchner funnel, and washed with water. When dry the solid weighed 3.45 g, mp (sinter 82°) 83°–88°, 70% of theory for $C_8F_{17}CH_2CH_2SCH_2CH_2SCH_2CH_2C_8F_{17}$. A 1.00-g sample was recrystallized from hot chloroform, that was first filtered while hot, from insoluble salt; 0.54 g, mp (sinter 90°) 92°–94°. The filtrate deposited 0.26 g of less pure solid. The original filtrate containing water and 1,2-dichloroethane (above) was separated into layers, and the organic layer evapd off to give white solid, mp 30°–33°, 1.18 g, 21.7% of theory for $C_8F_{17}CH_2CH_2SCH_2CH_2Cl$.

EXAMPLE 12

Reaction:

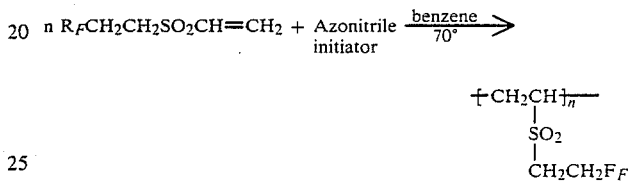

Polymerization of 2-(Perfluoroalkyl)ethanyl Vinyl Sulfones 2-(Perfluoroalkyl)ethanyl vinyl sulfone (1.00 g, 1.86 mmole, $R_F = 0.78\%$ $C_6F_{13}$, 95.6% $C_8F_{17}$ and 0.84% $C_{10}F_{21}$) and 0.100 g (0.61 mmole) of azo-bis-2-methylpropionitrile were heated under nitrogen in 20 ml of benzene while stirring by magnet bar in a flask under a reflux condenser. The initially clear solution became cloudy and formed a white suspension during the first 5 hours. After 17 hours of reaction the slurry was filtered, rinsed twice with benzene and dried, wt. 0.75 g, mp 96°–115°. An IR spectrum showed no vinyl absorption bands. Evaporation of the filtrate gave 0.32 g of soft solid.

EXAMPLE 13

Application of poly-2-(Perfluoroalkyl)ethanyl Vinyl Sulfone to Paper

A solution of 0.1004 g of polymer of Example 12 in 5.0 ml of acetone was slightly cloudy. It was filtered through a Whatman filter paper and dried. The filtrate remained cloudy. The filtrate was similarly drawn through another filter paper, and dried, with an increase in wt. of 9.8%. Both papers were highly repellent to water, to cooking oil and to toluene. The drops formed very high contact angle drops on the surface, did not spread or wet the surface and did not penetrate the paper. This results indicate that the polymer gave a coating on paper that was both hydrophobic and oleophobic.

EXAMPLE 14

Reaction:

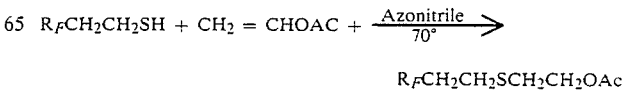

5-(Perfluorooctyl)ethanyl-3-thiapentan-1-ol Acetate

A glass pressure tube was charged with 2-(perfluorooctyl)ethanethiol (24.0 g, 50.0 mmole), vinyl acetate (redistilled, 4.30 g, 55.0 mmole) and azo-bis-2-methylpropionitrile (0.0821 g, 0.500 mmole). The tube was cooled to −78° C., evacuated and filled with nitrogen three times, and sealed. The tube was heated in a stirred oil bath at 70° for 12 hours, cooled and the cloudy, colorless liquid distilled. Forerun, bp 93°–110°/1.75 mm, 2.51 g, that contained unreacted thiol (0.71 g) and the desired acetate product (0.71 g), was collected. Then, the acetate, bp 106°–108°/0.75 mm, $n^{25}_D1/3628$, 95.4% pure by GC, was taken. The total yield of the acetate was 25.4 g, 89.7% of theory. The residue (0.66 g) was chiefly initiator-derived products. The cold trap contained 0.96 g of vinyl acetate and a little diethyl ether used to rinse the reaction vessel. The infrared spectrum of the acetate showed the C=O band at 1740 cm$^{-1}$. The NMR spectrum gave proton resonances at 2.00 ppm, a singlet, 3 protons, CH$_3$; at 2.75 ppm, a complex multiplet, 6 protons, (CH$_2$)$_2$SCH$_2$; and at 4.20 ppm, triplet, (J=7 Hz), 2 protons, CH$_2$O$_2$C—. These data are in accord with the structure of the title compound.

Anal. Calcd for C$_{14}$H$_{11}$F$_{17}$O$_2$S: C, 29.7; H, 2.0: F, 57.0. Found: C, 29.8; H, 2.0; F, 57.7.

EXAMPLE 15

5-(Perfluorohexyl)ethanyl-3-thiapentan-1-ol Acetate

A 100 ml, rb flask was charged with 2-(perfluorohexyl)-ethanethiol (redistilled, bp 73°/32 mm, 26.61 g, 70.0 mmole) and azo-bis-2-methylpropionitrile (0.150 g, 0.91 mmole), purged with nitrogen, and heaed in a bath at 65°–75° while stirring by magnet bar. Vinyl acetate (7.14 g, 82.5 mmole) was added during 40 minutes at 65°–72°, and stirring under nitrogen continued at 75° for 17 hours. The reaction mixture was distilled, giving a forerun, bp 68°–100°/11 mm, 1.00 g (mostly unreacted thiol; and the desired acetate bp 108°–113°/3.6 mm, 30.2 g, $n^{25}_D1.3692$. GC analysis showed a purity of 99.7%. A residue of 0.77 g and cold trap liquid of 0.51 g were obtained. The total yield of acetate was 30.7 g, or 99.7% of theory. Infrared and NMR spectra were consistent.

Anal. Calcd for C$_{12}$H$_{11}$F$_{13}$O$_2$S: C, 30.9; H, 2.38; F, 53.0; S, 6.88. Found: C, 31.1; H, 2.3; F, 53.4; S, 6.7.

EXAMPLE 16

Reaction:

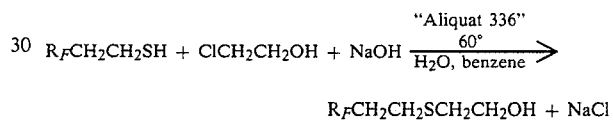

2-(Perfluorohexyl)ethanyl 2-Acetoxyethanyl Sulfone (5-Perfluorohexyl)ethanyl-3-thiapentan-1-ol acetate (46.85 g, 0.100 mole) stirred by magnet bar, was added acetic acid (75 ml) and acetic anhydride (25 ml) at 35°. While cooling with a bath at 20°, hydrogen peroxide (8.16 g, 0.24 mole, 30.1 ml of 27% by wt., aqueous solution) was added in part (10 ml) at 35°–42° during a half hour. Exothermic reaction occurred, and the bath temperature was raised to 38°–40°. Hydrogen peroxide (remaining 20 ml) was added slowly during one hour, while raising the bath temperature to 60°. The mixture was stirred at 60° for 15 hours. A sample that was precipitated into water gave a thick gel. Severe foaming occurred when evaporation in a rotary evaporator was attempted at reduced pressure. Thus, the solvent was distilled with great care in a packed column, bp 30°/25 mm. The residue, 51.03 g, was dried in vacuo over phosphoric anhydride at 20 mm for 18 h, and weighed 43.58 g, 88.2% of theory for 2-(perfluorohexyl)ethanyl 2-acetoxyethanyl sulfone. A sample melted at 62°–64°, and recrystallized from carbon tetrachloride had mp 63°–64°. The infrared spectrum gave bands at 3450–3200 (weak, OH), 1750 (C=O), and at 1300–1250, 1095, 1080, 1050 and 960 cm$^{-1}$. The NMR spectrum gave proton resonances at 2.10 ppm, (CH$_{3A}$); at 2.70 ppm, broad, complex multiplet, 2 protons (CH$_{2B}$); at 3.34 ppm, broad, complex multiplet, 4 protons (CH$_{2C}$ and CH$_{2D}$); at 4.15 ppm, a triplet, about 0.2 proton (CH$_{2E}$OH); and at 4.52 ppm, a triplet, about 0.8 proton CH$_{2E}$OAc). Some hydrolysis of the acetate ester was probably responsible for the formation of alcohol in the sample, R$_F$CH$_{2B}$CH$_{2C}$SO$_2$CH$_{2D}$CH$_{2E}$O$_2$CCH$_{3A}$.

Anal. Calcd for C$_{12}$H$_{11}$F$_{13}$O$_4$S: C, 28.9: H, 2.2; F, 49.6; S, 6.4. Found C, 28.4; H, 2.1; F, 50.1; S, 7.1.

EXAMPLE 17

Reaction:

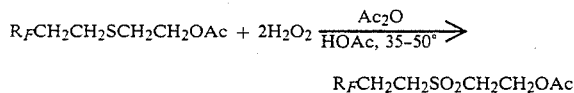

5-(Perfluorohexyl)-3-thiapentanol

In a 300 ml, rb, 3-n flask fitted with a nitrogen inlet, a constant rate dropping funnel and immersed in a constant temperature oil bath at 60°, was placed R$_F$CH$_2$CH$_2$SH (R$_F$=C$_6$F$_{13}$, 97.6%; C$_8$F$_{17}$, 1.3%; 38.0 g, 23.0 ml, 0.100 mole), 2-chloroethanol (16.1 g, 0.200 mole), tridecylmethylammonium chloride (0.25 g, 0.56 mole, "Aliquat 336", General Mills), and benzene (25 ml). A solution of sodium hydroxide (6.00 g, 0.150 mole) in water (50 ml) was added slowly during a half hour, while stirring by means of a magnet bar. At the beginning a purple color appeared which disappeared after 2 hours. The aqueous layer had a pH of 8–9. A sample was taken after 6 h, and stirring continued for 24 hours total time. A second sample was taken. The samples were converted to trimethylsilyl derivatives by reaction with BSTFA and GC analysis run: 5-ft "W-98" silicone oil, 43 ml/min of helium, 150° for five min, then 250°. Only peaks for homologs of the product were present at 9.6, 10.6 and 11.0 min. The layers were separated, the aqueous layer extracted twice with benzene (10 ml), rinsed with water and dried over MgSO$_4$. The benzene was removed by rotary evaporator, leaving 40.1 g of viscous oil (94.5% of theory not including samples) for C$_6$F$_{13}$CH$_2$CH$_2$SCH$_2$CH$_2$OH. An NMR spectrum was consistent, showing proton resonances at 2.38 ppm, a complex multiplet, 2 protons area, CH$_{2A}$; at 2.75 ppm, a complex multiplet, 4 protons, CH$_{2B}$ CH$_{2(C)}$; and at 3.67 ppm, a pseudo-q, 2 protons, CH$_{2(D)}$ for R$_F$CH$_{2A}$CH$_{2B}$SCH$_{2C}$CH$_{2D}$OH.

Anal. Calcd for C$_{10}$H$_9$F$_{13}$OS: C, 28.3; H, 2.14; F, 58.2; S, 7.56. Found: C, 28.6; H, 2.14; F, 58.3; S, 7.7.

EXAMPLE 18

5-(Perfluoroalkyl)-3-thia-pentanol

In the same manner as in Example 17, $R_fCH_2CH_2SH$ ($R_F=C_6F_{13}$, 12.7%; $C_8F_{17}$, 82.7%; $C_{10}F_{21}$, 3.3%; and $C_{12}H_{23}$, 0.96%; 65.0 g, 0.140 mole), 2-chloroethanol (22.54 g, 0.2799 mole), "Aliquat 336" (0.30 g, 0.67 mmole), sodium hydroxide (8.44 g, 0.211 mole), benzene (50 ml) and water (100 ml) at 60°, gave $R_fCH_2CH_2SCH_2CH_2OH$ ($R_F=C_6$, $C_8$, $C_{10}$ and $C_{12}$) as a precipitated white solid. When dry ($P_2O_5$) in vacuo, it weighed 69.11 g and contained sodium chloride that would not dissolve by water washing. A portion (10-g.) was extracted into hot carbon tetrachloride, filtered from insol. salt (0.45 g), and cooled; 6.65 g, mp 68°–71°, and subsequent fractions, a total of 9.22 g, were recovered. The remaining impure product was dissolved in anhydrous diethyl ether, filtered (3.67 g insoluble solid), and the ether removed; 53.8 g of solid was obtained that was used for analysis and subsequent reactions. GC analysis gave title compounds: $C_6$, 10.0%; $C_8$, 84.3%, $C_{10}$, 4.8% and $C_{12}$, 0.96%. An NMR spectrum was consistent for the structure of $R_fCH_2CH_2SCH_2CH_2OH$. The total product recovered was 62.6 g, 85.3% of theory.

EXAMPLE 19

5-(Perfluorohexyl)-3-thia-pentanol Acetate $C_6F_{13}CH_2CH_2SCH_2CH_2OH$ (40.1 g, 0.094 mole, undistilled), acetic anhydride (16.2 g, 0.15 mole) and pyridine (0.98 g, 12.4 mmole) was heated at 65°–66° for 4 hours and 89° for 17 hours under total reflux. A sample after 4 hours showed incomplete reaction and after 17 hours, only a trace of $C_6F_{13}CH_2CH_2SCH_2CH_2OH$ was present (GC analysis). The product was washed with saturated sodium bicarbonate (20 ml), extracted into ether, dried and the solvent removed by distillation; wt. 47.77 g. Total product was 49.3 g, 100% of theory. NMR was consistent for structure: proton resonances at 2.03 ppm, 3 protons, s, $CH_3$; at 2.42 ppm, multiplet, 2 protons, $CH_{2A}$; at 2.78 ppm, multiplet, 4 protons, $CH_{2A}$; at 2.78 ppm, multiplet, 4 protons, $CH_{2B}$ and $CH_{2C}$; and at 4.24 ppm, t, 2 protons $CH_{2D}$ for $C_6F_{13}CH_{2A}CH_{2B}SCH_{2C}CH_{2D}O_2CCH_3$.

Anal. Calcd for $C_{12}H_{11}F_{13}SO_2$: C, 30.9; H, 2.38; F, 53.0; S, 6.88. Found: C, 31.1; H, 2.3; F, 53.4; S, 6.7.

EXAMPLE 20

5-(Perfluorooctyl)-3-thia-pentanol Acetate $C_8F_{17}CH_2CH_2SCH_2CH_2OH$ (60 g, 0.11 mole, crude product, $C_8=95.6\%$) and acetic anhydride (15 g, 0.15 mole) (no pyridine) was heated at 80° for 17 hours, the volatile material removed by rotary evaporator; wt. 64.4 g, 100% of theory. IR: no OH but strong carbonyl band at 1735 cm$^{-1}$. GC showed traces of impurities and chiefly the desired acetate. NMR was consistent with the structure.

Anal. Calcd for $C_{14}H_{11}F_{17}SO_2$: C, 29.7; H, 1.96; F, 57.0; S, 5.66. Found: C, 29.7; H, 2.0; F, 55.8.

EXAMPLE 21

2-(Perfluorooctyl)ethanyl 2-Acetoxyethanyl Sulfone

The product of Example 20 (6.00 g, 0.0106 mole, crude product) was dissolved in acetone (50 ml), and water (10 ml) was added, followed by 3 ml of 0.3M ammonium molybdate solution, at 23°. A precipitate formed that dissolved when hydrogen peroxide (1.70 g, 0.050 mole, 6.3 ml, 27%) was added in portions during 15 mi. The temp. rose to 31° and the mixture, while stirring by magnet bar, set up to a crystalline solid mass. After 1 h at 30°, the mixture was heated to 46°–48° for 1 hour, and cooled to 25° C. A sample gave mp 96°–100° (decomposed). The reaction mixture was worked up by adding 50 ml of water and extracting into chloroform (50 ml). The clear, colorless chloroform solution was dried (MgSO$_4$), filtered and evaporated off in rotary evaporator to 50°/15 mm. The solvent came off at first, but then the product began to sublime into the condenser. The material was dissolved out with acetone and evaporated off, 4.55 g, 72% of theory, mp 93°–96° (capillary tube placed in the bath at 93°).

IR showed carbonyl 1740 cm$^{-1}$, and bands at 1090,1045,960; 845,800; 775,750,710; 650,610,590,580,560,530,500 cm$^{-1}$.

Anal. Calcd for $C_{14}H_{11}F_{17}SO_4$: C, 28.1; H, 1.85; F, 54.0; S, 5.36. Found: C, 28.2; H, 1.7; F, 54.2; S, 5.8.

What is claimed is:

1. A compound of the formula

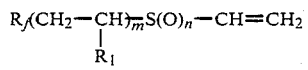

wherein
$R_f$ is perfluoroalkyl of 4 to 12 carbon atoms,
$R_1$ is hydrogen,
m is 1, and
n is 1 or 2.

2. A compound according to claim 1, wherein $R_f$ is perfluoroalkyl of 4 to 12 carbon atoms.

3. A compound according to claim 1, wherein $R_1$ is hydrogen.

4. A compound according to claim 1, wherein n is 2.

* * * * *